(12) United States Patent
Hunt

(10) Patent No.: US 11,058,771 B2
(45) Date of Patent: Jul. 13, 2021

(54) VASCULAR ULCER TREATMENT

(71) Applicant: BOSTON SCIENTIFIC SCIMED, INC., Maple Grove, MN (US)

(72) Inventor: Matthew Hunt, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 154 days.

(21) Appl. No.: 15/893,092

(22) Filed: Feb. 9, 2018

(65) Prior Publication Data

US 2018/0228896 A1   Aug. 16, 2018

Related U.S. Application Data

(60) Provisional application No. 62/457,538, filed on Feb. 10, 2017.

(51) Int. Cl.

| | |
|---|---|
| *A61K 41/00* | (2020.01) |
| *A61K 9/70* | (2006.01) |
| *A61K 47/69* | (2017.01) |
| *A61P 9/00* | (2006.01) |
| *A61K 31/315* | (2006.01) |
| *A61P 17/02* | (2006.01) |
| *A61K 31/198* | (2006.01) |
| *A61L 15/38* | (2006.01) |
| *A61L 15/18* | (2006.01) |
| *A61K 9/51* | (2006.01) |
| *A61K 9/00* | (2006.01) |

(52) U.S. Cl.
CPC .............. *A61K 41/00* (2013.01); *A61K 9/009* (2013.01); *A61K 9/5115* (2013.01); *A61K 9/703* (2013.01); *A61K 9/7023* (2013.01); *A61K 31/198* (2013.01); *A61K 31/315* (2013.01); *A61K 47/6903* (2017.08); *A61K 47/6923* (2017.08); *A61K 47/6953* (2017.08); *A61L 15/18* (2013.01); *A61L 15/38* (2013.01); *A61P 9/00* (2018.01); *A61P 17/02* (2018.01)

(58) Field of Classification Search
CPC .... A61K 9/5115; A61K 47/6923; A61K 9/00; A61K 9/0009; A61P 9/00
See application file for complete search history.

(56) References Cited

U.S. PATENT DOCUMENTS

| | | | |
|---|---|---|---|
| 6,106,866 A * | 8/2000 | Ranney | A61K 49/12 424/489 |
| 8,709,393 B2 | 4/2014 | McAnulty et al. | |
| 2003/0032995 A1 | 2/2003 | Handy et al. | |
| 2005/0106100 A1* | 5/2005 | Harris | A61K 51/08 424/1.49 |
| 2010/0183504 A1 | 7/2010 | Chen | |
| 2011/0213286 A1* | 9/2011 | Riesinger | A61F 13/0203 602/43 |

FOREIGN PATENT DOCUMENTS

| | | |
|---|---|---|
| EP | 2262510 A1 | 12/2010 |
| WO | 2015/157530 A2 | 10/2015 |

OTHER PUBLICATIONS

Achilli et al., "Fe3O4@SiO2 core-shell nanoparticles for biomedical purposes: adverse effects on blood cells", Biomaterials Science, 4:1417-1421, The Royal Society of Chemistry, 2016.
Benz, "Superparamagnetism: Theory and Applications Discussion of Two Papers on Magnetic Nanoparticles", pp. 1-27, Dec. 14, 2012.
Galateanu et al., "In Vitro Studies of Bacterial Cellulose and Magnetic Nanoparticles Smart Nanocomposites for Efficient Chronic Wounds Healing", Stem Cells International, pp. 1-10, 2015.
Gibson et al., "MMPs Made Easy", Wounds International, 1(1):1-6, Nov. 2009.
Hankin et al., "Clinical and Cost Efficacy of Advanced Wound Care Matrices for Venous Ulcers", Journal of Managed Care Pharmacy, 18(5):375-84, Academy of Managed Care Pharmacy, Jun. 2012.
Jal, et al., "Chemical modification of silica surface by immobilization of functional groups for extractive concentration of metal ions", Talanta, 62:1005-1028, Elsevier B.V., 2004.
Kahn et al., "Determinants and Time Course of the Postthrombotic Syndrome after Acute Deep Venous Thrombosis", Annals of Internal Medicine, 149(10):698-707, Nov. 18, 2008.
Korrapati et al., "Recent advancements in nanotechnological strategies in selection, design and delivery of biomolecules for skin regeneration", Materials Science and Engineering C, 67:747-765, Elsevier B.V., 2016.
Krejner et al., "Modulation of matrix metalloproteinases MMP-2 and MMP-9 activity by hydrofiber-foam hybrid dressing—relevant support in the treatment of chronic wounds", Central European Journal of Immunology, 40(3): 391-394, 2015.
Oliveira-Silva et al., "Magnetic chelating nanoprobes for enrichment and selective recovery of metalloproteases from human saliva", Journal of Materials Chemistry B, 3:238-249, The Royal Society of Chemistry, 2015.

(Continued)

*Primary Examiner* — Johann R Richter
*Assistant Examiner* — Danielle Sullivan
(74) *Attorney, Agent, or Firm* — Seager, Tufte & Wickhem, LLP

(57) ABSTRACT

A patch for treating vascular ulcers caused by excessive enzymatic activity may include a substrate configured to span a vascular ulcer as well as a linking material that is disposed relative to the substrate and has an affinity for an enzyme involved in causing the vascular ulcer. A magnetic material may be coupled to the linking material. In some cases, the enzymes involved in causing the vascular ulcer may become coupled to the linking material and thus become coupled to the magnetic material so that that the enzymes can be removed by applying a magnetic field in the proximity of the vascular ulcer. The enzymes may include matrix metalloproteinases.

20 Claims, 9 Drawing Sheets

(56) References Cited

OTHER PUBLICATIONS

Prandoni et al., "The Long-Term Clinical Course of Acute Deep Venous Thrombosis", Annals of Internal Medicine, 125(1): 1-7, American College of Physicians, Jul. 1, 1996.
International Search Report and Written Opinion dated May 24, 2018 for International Application No. PCT/US2018/017697.

* cited by examiner

VASCULAR ULCER TREATMENT

CROSS-REFERENCE TO RELATED APPLICATIONS

This application claims the benefit of priority under 35 U.S.C. § 119 to U.S. Provisional Application Ser. No. 62/457,538, filed Feb. 10, 2017, the entirety of which is incorporated herein by reference.

TECHNICAL FIELD

The disclosure is directed to medical treatments and more particularly to medical treatments for venous ulcers, including topical applications for treating venous ulcers.

BACKGROUND

Post thrombotic syndrome (PTS) affects a number of patients with previous deep vein thrombosis (DVT). In some cases, these patients may develop vascular ulceration, including veinous ulceration and arterial ulceration. Of the known treatments for vascular ulceration, each has certain advantages and disadvantages. There is an ongoing need to provide alternate treatments for vascular ulceration, particularly for vascular ulceration resulting from previous DVT, as well as alternate products for treating vascular ulceration and methods for treating vascular ulceration.

SUMMARY

The disclosure is directed to several alternative designs, materials and methods of manufacturing medical device packaging, and uses thereof. In an example, the disclosure pertains to a kit for treating a vascular ulcer in which enzymatic activity contributes to formation of the vascular ulcer. The kit includes a first component configured to be positioned relative to the vascular ulcer and a second component that is configured to be positioned relative to the vascular ulcer subsequent to application of the first component. The first component includes a linking material having an affinity for an enzyme involved in formation of the vascular ulcer and a first magnetic material that is coupled to the linking material such that the enzyme within the vascular ulcer can become coupled to the linking material and become coupled to the first magnetic material. The second component includes a second magnetic material that is configured to attract the first magnetic material and attract the enzymes coupled to the first magnetic material via the linking material.

Additionally or alternatively, the first magnetic material may include magnetic nanoparticles.

Additionally or alternatively, the magnetic nanoparticles may have an average size range of about 3 to about 50 nanometers (nm).

Additionally or alternatively, the first component may further include a carrier, and the linking material may be dispersed relative to the carrier.

Additionally or alternatively, the carrier may be a topical gel.

Additionally or alternatively, the carrier may include a woven or nonwoven material forming an adhesive patch.

Additionally or alternatively, the enzyme may include a matrix metalloproteinase and the linking material may include a chelating agent that is configured to chelate a metal ion complexed by the matrix metalloproteinase.

Additionally or alternatively, the metal ion complexed by the matrix metalloproteinase may include calcium ions or zinc ions.

In another example, the disclosure pertains to a patch for treating vascular ulcers caused by excessive matrix metalloproteinases. The patch includes a substrate that is configured to span a vascular ulcer and a linking material that is disposed relative to the substrate and has an affinity for matrix metalloproteinases. A magnetic material is coupled to the linking material. The matrix metalloproteinases within the vascular ulcer can become coupled to the linking material and become coupled to the magnetic material so that that the matrix metalloproteinases can be removed by applying a magnetic field in the proximity of the vascular ulcer.

Additionally or alternatively, the linking material may include a polydentate chelating agent having one or more binding sites available to couple with the magnetic material and one or more binding sites available to chelate a metal ion complexed by the matrix metalloproteinases.

Additionally or alternatively, the linking material may include ethylenediaminetetracetic acid (EDTA).

Additionally or alternatively, the EDTA may be bonded to the magnetic material by an intervening material.

Additionally or alternatively, the intervening material may include tetramethylsilane (TMS).

Additionally or alternatively, the magnetic material may include magnetic nanoparticles having an average size range of about 3 to about 50 nanometers (nm).

Additionally or alternatively, the substrate may further include a topical gel that is disposed relative to the substrate, and the linking material is dispersed within the topical gel.

Additionally or alternatively, the substrate may include a woven or nonwoven material, and the linking material is disposed on or within the woven or nonwoven material.

In another example, the disclosure pertains to a method of treating a vascular ulcer in which enzymatic activity contributes to formation of the vascular ulcer. A treatment material is disposed relative to the vascular ulcer, the treatment material including a linking material coupled with a magnetic material, the linking material configured to chelate a metal ion complexed by a matrix metalloproteinase. The treatment material is allowed to diffuse into the vascular ulcer so that the linking material has time to chelate the metal ion and couple to the matrix metalloproteinase. The vascular ulcer is subsequently subjected the vascular ulcer to an attractive magnetic force that draws the magnetic material and thus the chelated matrix metalloproteinase out of the vascular ulcer.

Additionally or alternatively, disposing a treatment material relative to the vascular ulcer may include disposing a patch including the treatment material over the vascular ulcer.

Additionally or alternatively, disposing a treatment material relative to the vascular ulcer may include providing a flow of a liquid carrier including the treatment material from a reservoir directly to the vascular ulcer.

Additionally or alternatively, subsequently subjecting the vascular ulcer to an attractive magnetic force may include placing a magnet over the vascular ulcer.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
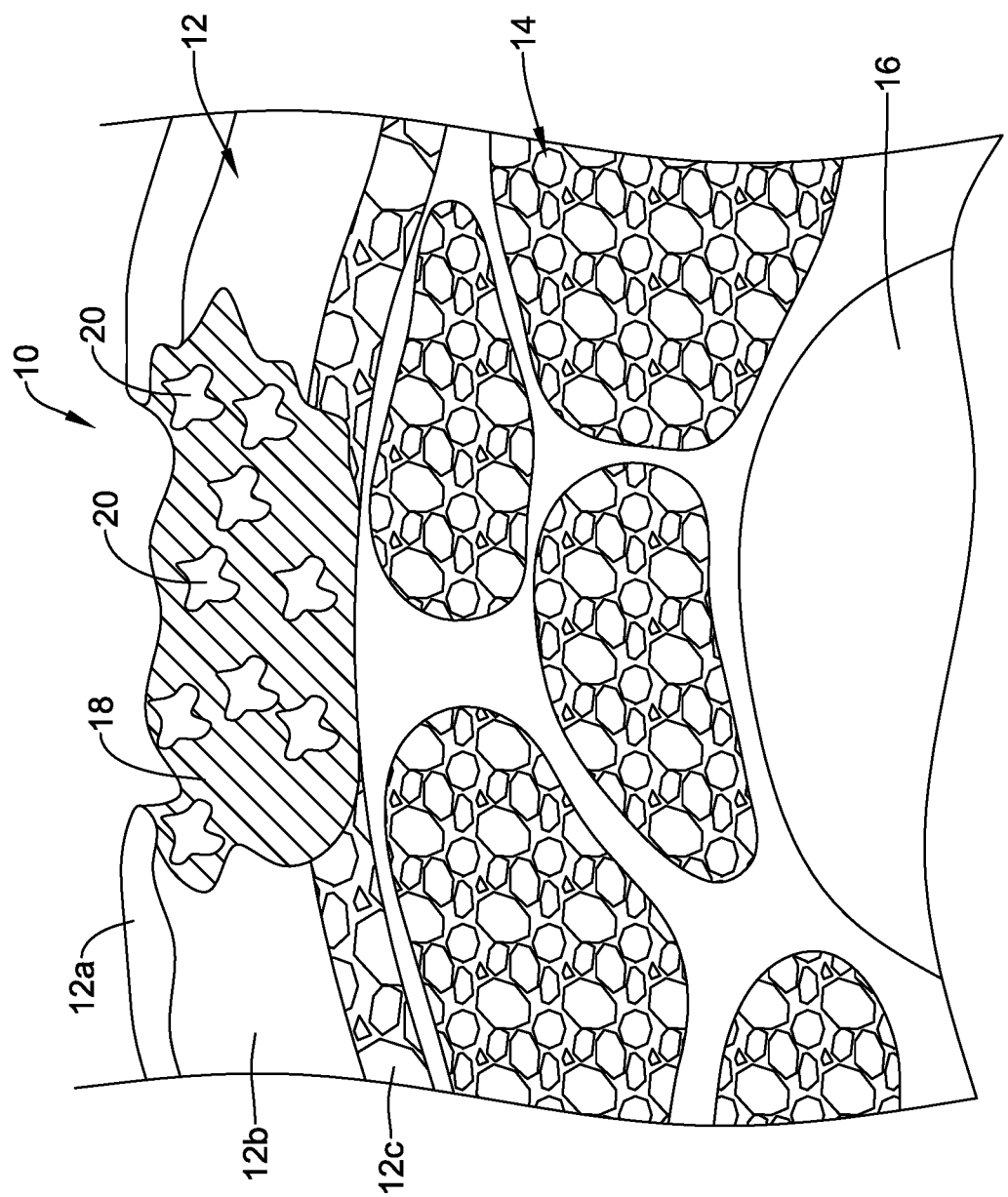
FIG. 1 is a schematic illustration of tissue layers including a vascular ulcer.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

In some cases, a patient may have a post thrombotic syndrome (PTS) subsequent to deep vein thrombosis (DVT). In some cases, for example, DVT can lead to PTS through several mechanisms, including residual obstruction, poor calf muscle-pump function, and reflux due to poor vein valve function. In some cases, PTS can cause venous hypertension and venous stasis, which originate in the deep veins at the site of dysfunction, but backup through the perforator veins to the level of venules and capillaries, much like a traffic jam. At the level of the capillaries and integumentary system, high pressure and stasis can lead to local inflammation and extravasation of erythrocytes out of the capillary walls. This, in turn, may lead to a host of problems encompassed in the condition of lipodermatosclerosis (LDS), which may eventually lead to venous stasis ulceration.

In some cases, one set of molecular agents that may be involved in driving the progression from the upstream problems of stasis and hypertension through LDS to ulceration are matrix metalloproteinases (MMPs). These are zinc-containing, calcium-dependent enzymes that degrade extracellular matrix proteins. The body also has endogenous MMP inhibitors known as TIMP, or tissue inhibitor of metalloproteinase. In the process leading to ulceration, reactive oxygen species increase the levels of MMPs through several pathways. An imbalance in the level of MMP to TIMP can lead to uncontrolled cleavage of extracellular matrix, which leads to the breakdown of skin and the formation of a venous ulcer. In some cases, targeting the elevated levels of MMP that drive the formation of venous can improve recovery rate from ulceration and potentially prevent ulcer formation at the onset of venous disease.

Accordingly, the disclosure is directed to addressing ulcer persistence and formation by providing patches, kits and methods for removing enzymes such as MMPs from an ulcerative wound. In some cases, the ulcerative wound may be considered as being a vascular ulcer. In some cases, the ulcerative wound may be considered as being a venous ulcer. In some instances, the ulcerative wound may be considered as being an arterial ulcer or even a pressure ulcer, depending on which vasculature had an initial problem.

In some cases, as will be discussed, MMPs may be removed from a wound site's extracellular fluid, or wound exudate, by providing a linking material that is coupled to a magnetic material. The linking material may, for example, either directly couple or bond to an enzyme such as an MMP, or the linking material may chelate a metal ion that is complexed with the MMP. Once the linking material has effectively coupled the magnetic material to the MMP, the magnetic material and MMP in combination may be removed from the wound exudate using a magnet. In some cases, the magnet may be extracorporeal, while in other cases the magnet may be positioned intravascularly. In some cases, reducing the relative level of MMP within the wound may slow or reverse tissue degeneration and enable healing. In some cases, a decrease in MMP level may result in decreased breakdown of collagen, elastin, and other ECM proteins. With lower levels of MMP, the endogenous levels of TIMP may sufficiently regulate remaining MMP activity.

FIG. 1 provides a schematic view of a vascular ulcer 10 formed within a skin layer 12. As seen in FIG. 1, the skin layer 12 lays atop a tissue and muscle layer 14 and a bone layer 16. While the skin layer 12 is schematically shown, it will be appreciated that human skin actually has a number of distinct layers. In some cases, the skin layer 12 may include an epidermis 12a, a dermis 12b and a hypodermis 12c. The bone layer 16 may for example represent a femur, if the vascular ulcer 10 is formed in a patient's upper leg, or may represent a tibia or fibula if the vascular ulcer 10 is formed in the patient's lower leg.

As illustrated, the vascular ulcer 10 includes wound exudate 18 and a number of schematically illustrated MMPs 20 disposed within the wound exudate 18. It will be appreciated that the MMPs 20 are greatly exaggerated in size for the purposes of being visible in FIG. 1. As illustrated, the vascular ulcer 10 extends just about all the way through the skin layer 12, having penetrated the epidermis 12a, the dermis 12b and the hypodermis 12c, but has not penetrated the tissue and muscle layer 14. In some cases, the vascular ulcer 10 may extend only part way through the skin layer 12. In some cases, the vascular ulcer 10 may extend at least partway into the tissue and muscle layer 14. In some cases, the vascular ulcer 10 may be sub-surface, having not penetrated outwardly through the epidermis 12a, and thus may more properly be referred to as a vascular lesion.

Figure 2:
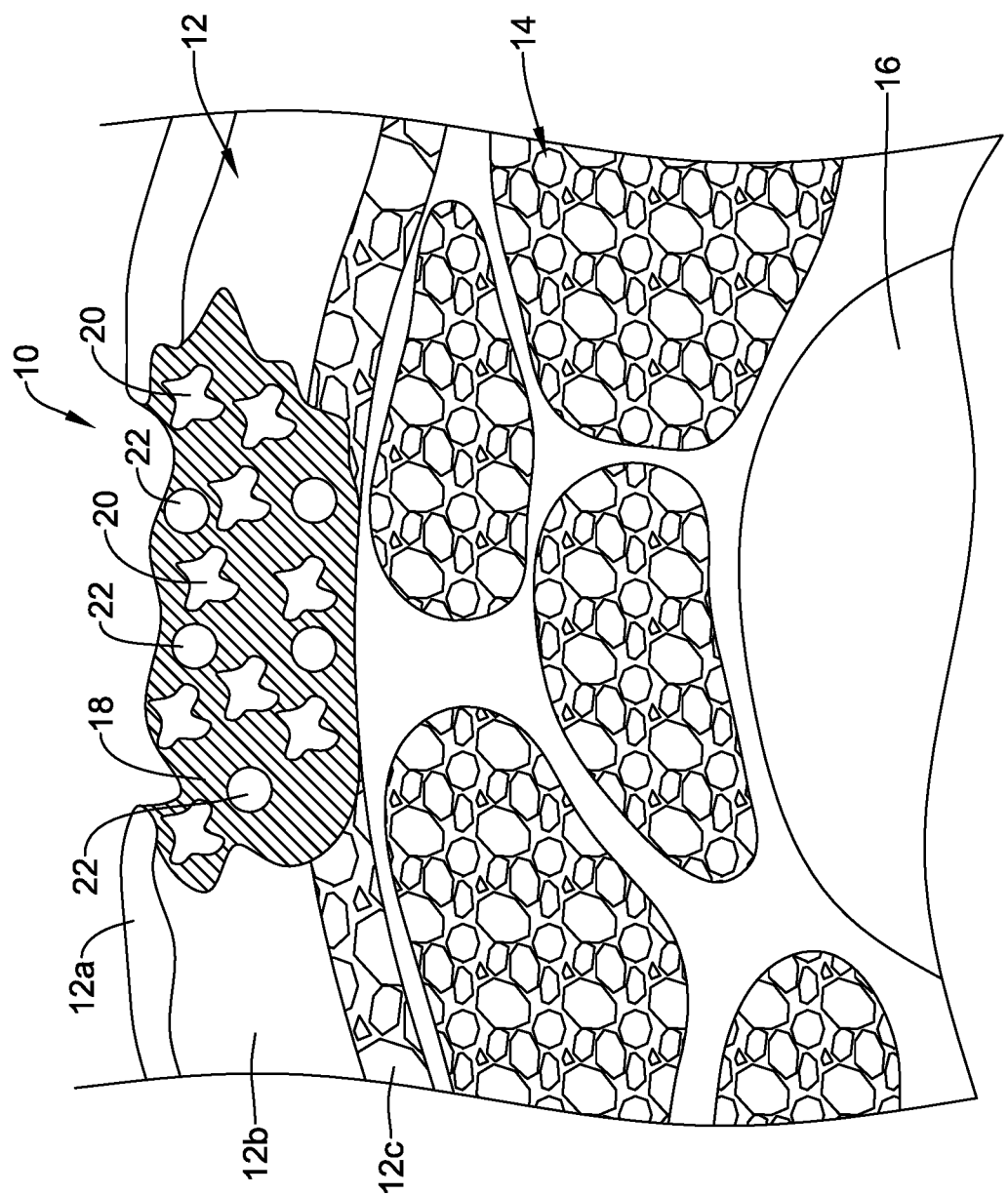
FIG. 2 is a schematic illustration of tissue layers including a vascular ulcer, illustrating an initial treatment step in accordance with an example of the disclosure.

Turning to FIG. 2, it can be seen that a plurality of treatment particles 22 have been added to the wound exudate 18. In some cases, the plurality of treatment particles 22 may be applied to the vascular ulcer 10 via application of a topical gel bearing the plurality of treatment particles 22. In some cases, the plurality of treatment particles 22 may be applied to the vascular ulcer 10 by applying a patch or other structure carrying the plurality of treatment particles 22. In either case, as can be seen in FIG. 2, the plurality of treatment particles 22 may be seen as having started to diffuse through the exudate 18.

In some cases, the plurality of treatment particles 22 may include a linking material that has an affinity for the enzymes involved, such as but not limited to MMP, that is coupled to a magnetic material. The linking material may become coupled to the MMP via a variety of different mechanisms, although in some cases, the linking material may chelate a metal ion that is complexed by the MMP. In some cases, the linking material may be a chelating agent such as a polydentate chelating agent. A polydentate chelating agent may be considered as having one or more binding sites that are available to be directly or indirectly coupled with the magnetic material as well as one or more binding sites that are available to chelate a metal ion that is complexed by the MMP.

As an example, a tetradentate chelating agent such as ethylenediaminetetracetic acid (EDTA) may be used. EDTA has the chemical structure shown below:

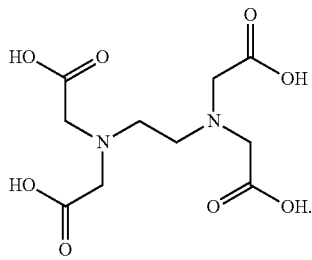 [SMILES: O=C(O)CN(CCN(CC(=O)O)CC(=O)O)CC(=O)O]

As another example, the chelating agent may be diethlenetriaminepentaacetic acid (DTPA). DTPA has the chemical structure shown below:

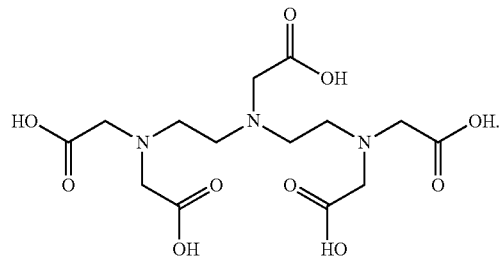 [SMILES: O=C(O)CN(CCN(CC(=O)O)CC(=O)O)CCN(CC(=O)O)CC(=O)O]

As another example, the chelating agent may be 1,2-bis(o-aminophenoxy)ethane-N,N,N',N'-tetraacetic acid (BAPTA). BAPTA has the chemical structure shown below:

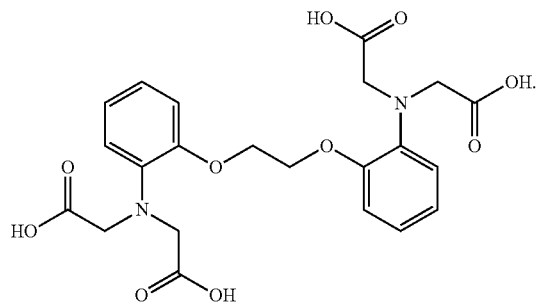 [SMILES: O=C(O)CN(CC(=O)O)c1ccccc1OCCOc1ccccc1N(CC(=O)O)CC(=O)O]

As another example, the chelating agent may be ethylene glycol-bis(β-aminoethyl ether)-N,N,N',N'-tetraacetic acid (EGTA). EGTA has the chemical structure shown below:

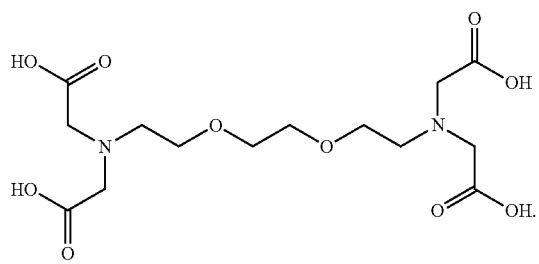 [SMILES: O=C(O)CN(CCOCCOCCN(CC(=O)O)CC(=O)O)CC(=O)O]

In some cases, the linking material such as EDTA may bind directly to a magnetic material. In some cases, the magnetic material may be coated with silica, and the linking material may be bound to the silica. In some instances, particularly if the linking material does not have a reactive functional group that can chemically bond to the silica substrate, the linking material may instead be physically adsorbed to the silicate substrate.

In some cases, the linking material may indirectly bind to the magnetic material by bonding to an intermediate material that itself binds to the magnetic material. Examples of suitable linking materials include diethylenetriamine (DETA) salicylaldehyde silica, DETA naphthaldehyde silica, DETA bis-naphthaldehyde silica, DETA bis-salicylaldehyde silica, propylthioethylamine silica, mercapto silica, silicon 3-aminopropyltriethoxysilane, 2,4-D immobilized silica, carboxyhydrazone functionalized silica, 3-hydroxy-2-methyl-1,4-napthaquinone immobilized silica, 5-amino-1,3,4-thiadizole-2-thiol modified silica, aminopropyl silica, and N-5-azido-2-nitrobenzoyloxysuccinimide modified silica.

As a particular example, a silane material such as tetramethoxylsilane (TMS) may be used to link the EDTA (or other linking material) to the magnetic material. The structure of TMS is shown below:

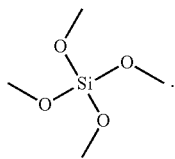

In some cases, the chelating agent may be attached to a short hydrocarbon chain in order to mitigate stearic hindrance that could otherwise occur. In some instances, this may be accomplished by using 3-chloropropyltriethoxysilane, the structure of which is shown below:

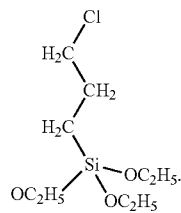

Figure 7:
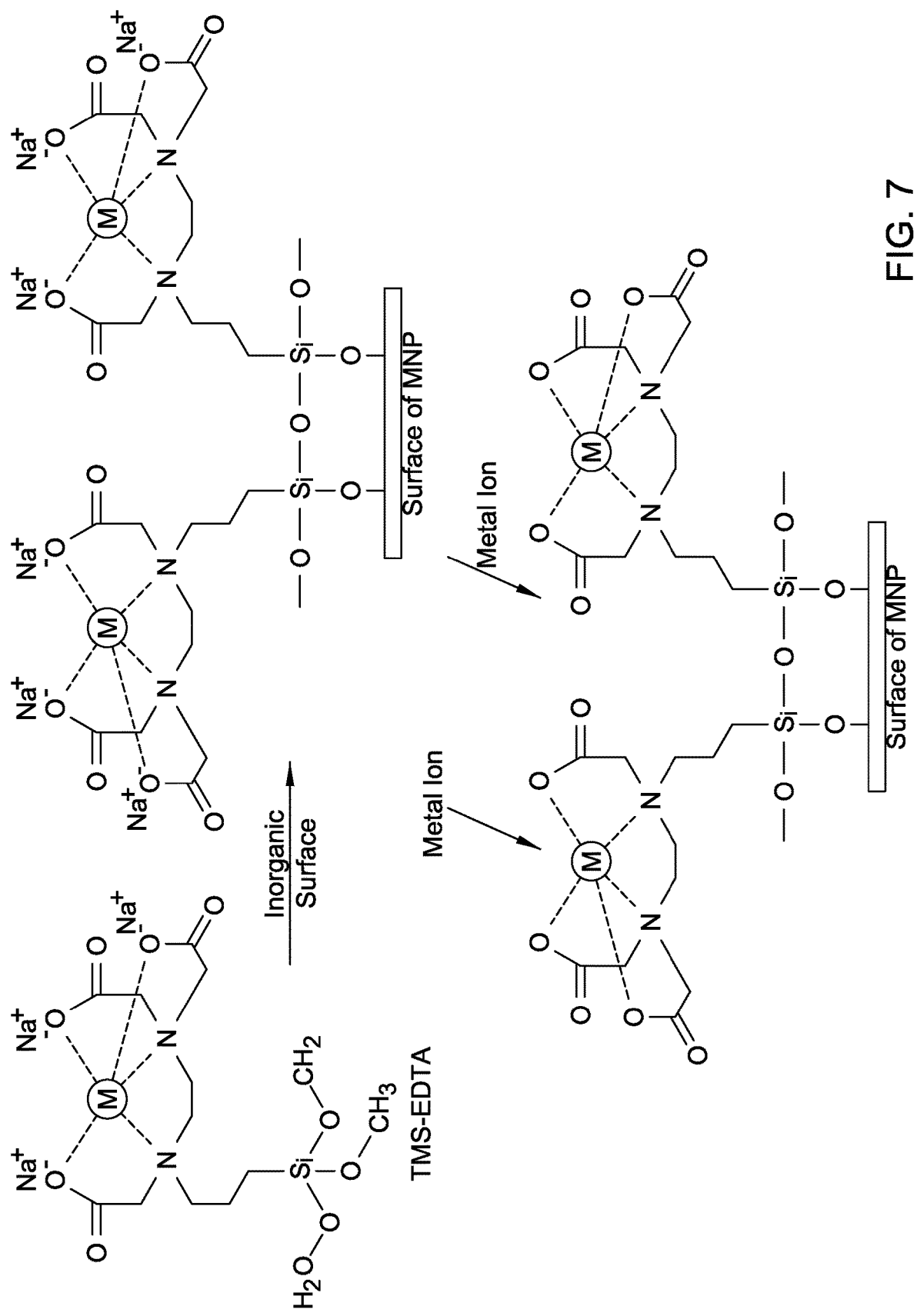
FIG. 7 is a schematic illustration of how a linking material can chelate a metal ion involved in enzymatic activity.

As noted, the treatment particles 22 include a magnetic material. In some cases, the magnetic material may include magnetic nanoparticles (MNP). These are spherical particles with a diameter in the range of 3 to 50 nanometers (nm). In some cases, magnetic nanoparticles in this size range may be considered as being superparamagnetic, meaning that under some circumstances the magnetic nanoparticles may change polarity as a result of particular temperature changes. In some cases, magnetic nanoparticles may be made of magnetite, which has the chemical formula $Fe_3O_4$, and which includes iron in both the Fe(III) state and the Fe(II) state. As will be discussed subsequently, FIG. 7 provides an example of the chemistry involved in forming the plurality of treatment particles 22.

Figure 3:
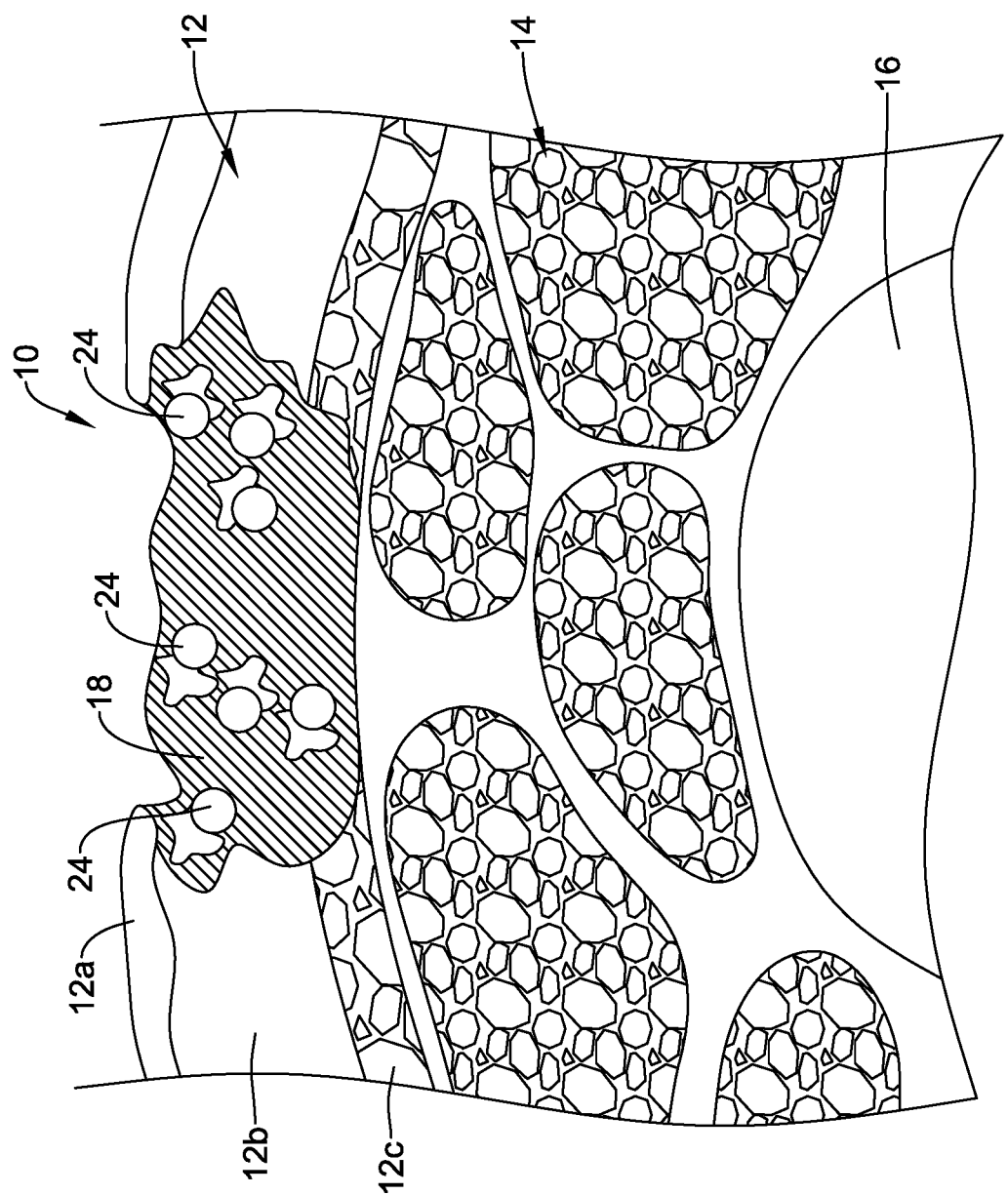
FIG. 3 is a schematic illustration of tissue layers including a vascular ulcer, illustrating diffusion during the initial treatment step shown in FIG. 2.

Turning to FIG. 3, it can be seen that the plurality of treatment particles 22 shown in FIG. 2 has diffused into the wound exudate 18 and have been coupled to the MMPs 20 to form MMP-MNP combinations 24, in which a linking material is coupled to the MMP 20, such as by chelating a metal ion complexed by the MMP 20, and is also coupled either directly to the MNP or indirectly to the MNP via an intermediate material. At this point, the MMP-MNP combinations 24 may be removed from the vascular ulcer 10 via application of a magnetic force.

Figure 4:
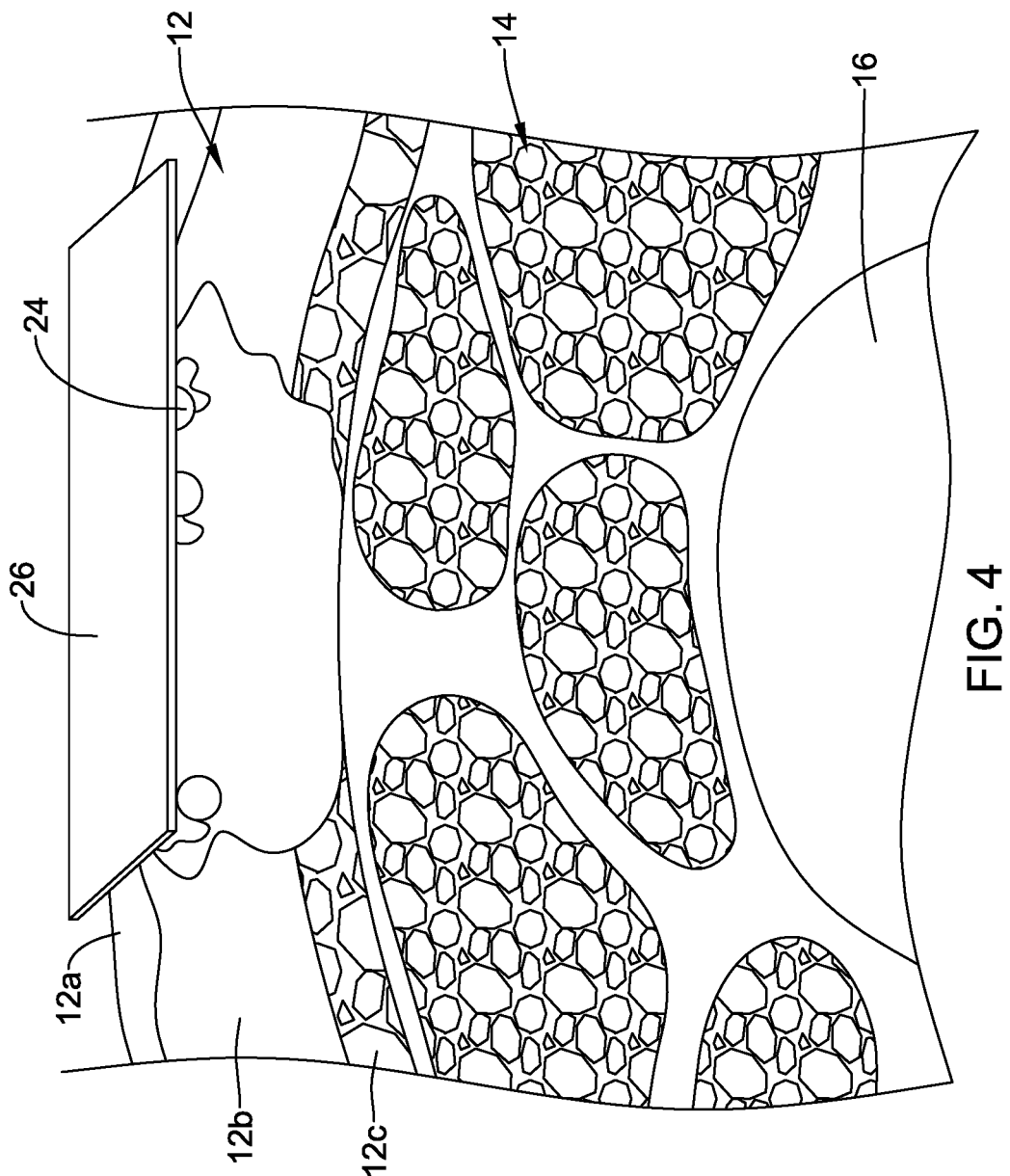
FIG. 4 is a schematic illustration of tissue layers including a vascular ulcer, illustrating a subsequent treatment step.

As seen in FIG. 4, a magnet 26 may be placed in proximity to the vascular ulcer 10. The magnetic force emanating from the magnet 26 provides an attractive force that pulls the MMP-MNP combinations 24 towards the magnet 26 and thus out of the vascular ulcer 10. In some cases, a first magnet 26 may become saturated with MMP-MNP combinations 24. In such cases, the first magnet 26 may be removed and a second or subsequent magnet 26 may be placed in proximity to the vascular ulcer 10.

Figure 5:
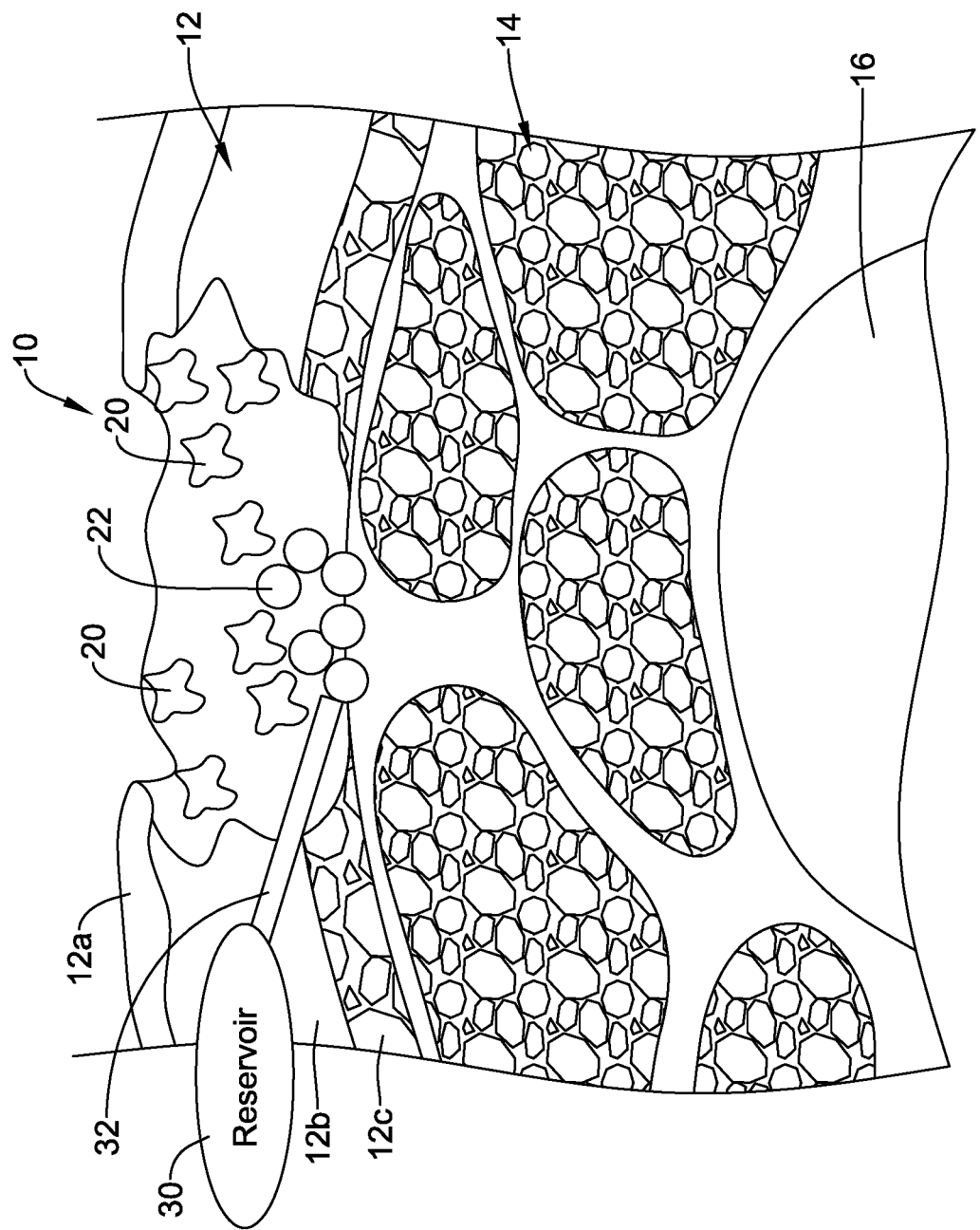
FIG. 5 is a schematic illustration of tissue layers including a vascular ulcer, illustrating an initial treatment step in accordance with another example of the disclosure.
Figure 6:
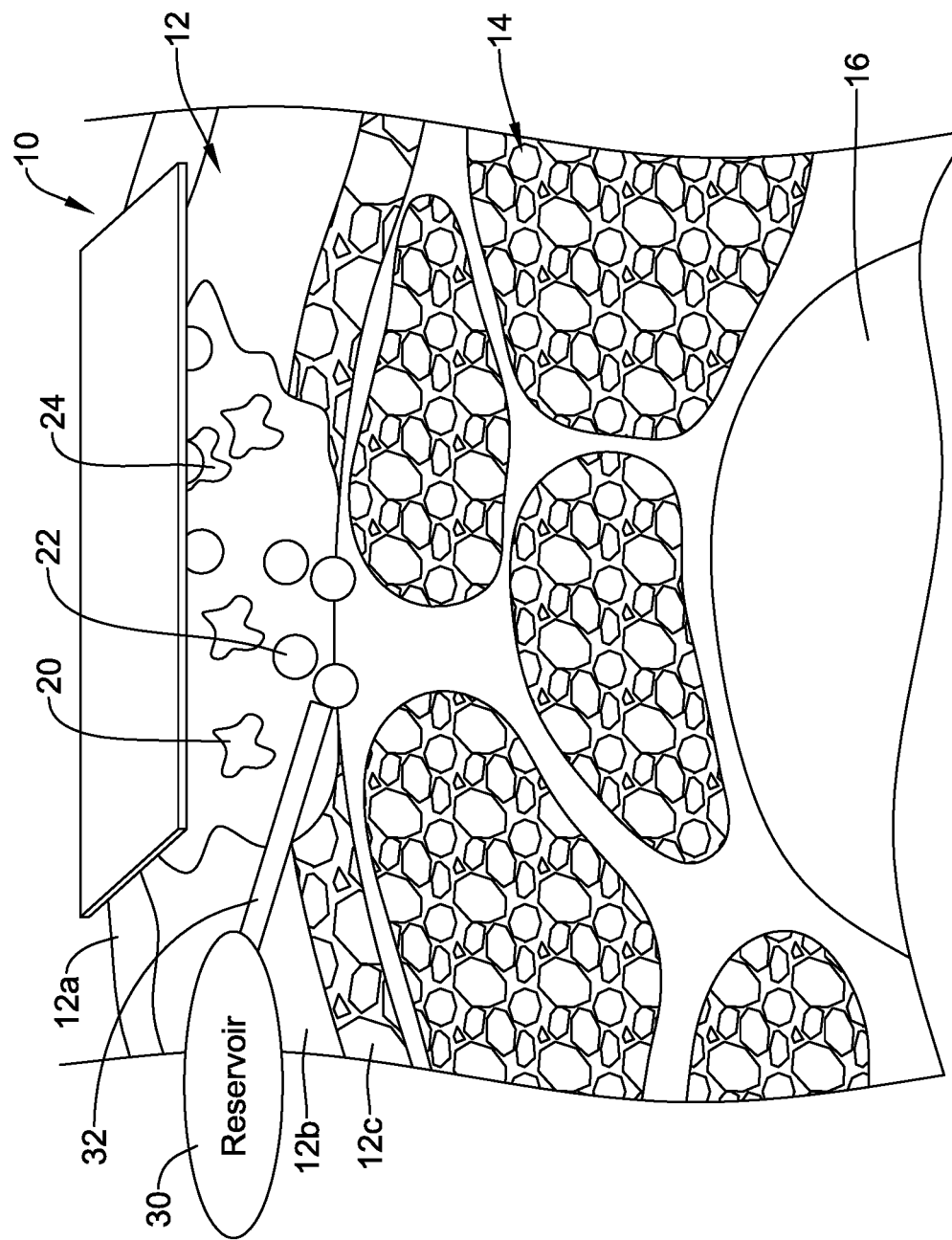
FIG. 6 is a schematic illustration of tissue layers including a vascular ulcer, illustrating a treatment step subsequent to that shown in FIG. 5.

In some cases, a plurality of treatment particles 22 may be applied in a continuous or semi-continuous process, rather than a one-time application as shown in FIG. 2, FIG. 3 and FIG. 4. FIG. 5 and FIG. 6 show an example in which a plurality of treatment particles 22 may be provided via a reservoir 30. In some cases, the reservoir 30 may include a tube 32 that may more particularly direct the plurality of treatment particles 22 into the vascular ulcer 10. In some cases, the reservoir 30 may provide treatment particles 22 on a gravity-feed basis, or perhaps by a concentration gradient between the contents of the reservoir 30 and that of the wound exudate 18. In some cases, the reservoir 30 may be positioned so that the reservoir 30 may be squeezed or compressed in order to facilitate the flow of treatment particles 22 from the reservoir 30 and into the wound exudate 18. In some cases, the reservoir 30 may be extracorporeal, such as like an insulin pump, and the tube 30 may extend through the skin layer 12 to provide the treatment particles 22 into the wound exudate 18.

As seen in FIG. 5, the treatment particles 22 have entered the vascular ulcer 10 but have not substantially diffused into the wound exudate 18 and thus towards the MMPs 20. In FIG. 6, it can be seen that diffusion has begun, and some of the treatment particles 22 have been coupled to the MMPs 20 to form MMP-MNP combinations 24. Application of the magnet 26, which may occur at the same time as placement of the reservoir 30, or possibly subsequent to placement of the reservoir 30 to allow for diffusion time, will attract the MMP-MNP combinations 24 towards the magnet 26 and thus out of the vascular ulcer 10. In some cases, a first magnet 26 may become saturated with MMP-MNP combinations 24. In such cases, the first magnet 26 may be removed and a second or subsequent magnet 26 may be placed in proximity to the vascular ulcer 10.

FIG. 7 provides an illustrative but non-limiting example of the chemistry that may be used to form the treatment particles 22. As can be seen in FIG. 7, the reaction scheme begins with TMS and EDTA covalently bound to each other, and then being exposed to an inorganic surface such as a surface of a magnetic nanoparticle. This secures the linking material (the EDTA) to the magnetic material via an intermediate material (the TMS). Once the linking material is coupled to the magnetic material, the linking material is able to chelate a metal ion. Because the metal ion is complexed with an MMP (not shown) in FIG. 7, this effectively couples the MMP to the MNP, and application of a magnetic force may be used to pull the MNPs (and thus the MMPs) out of the vascular ulcer 10. It will be appreciated that this reaction scheme is merely illustrative, as a variety of different linking materials and/or a variety of different intermediate materials may be used in forming the treatment particles 22.

Figure 8:
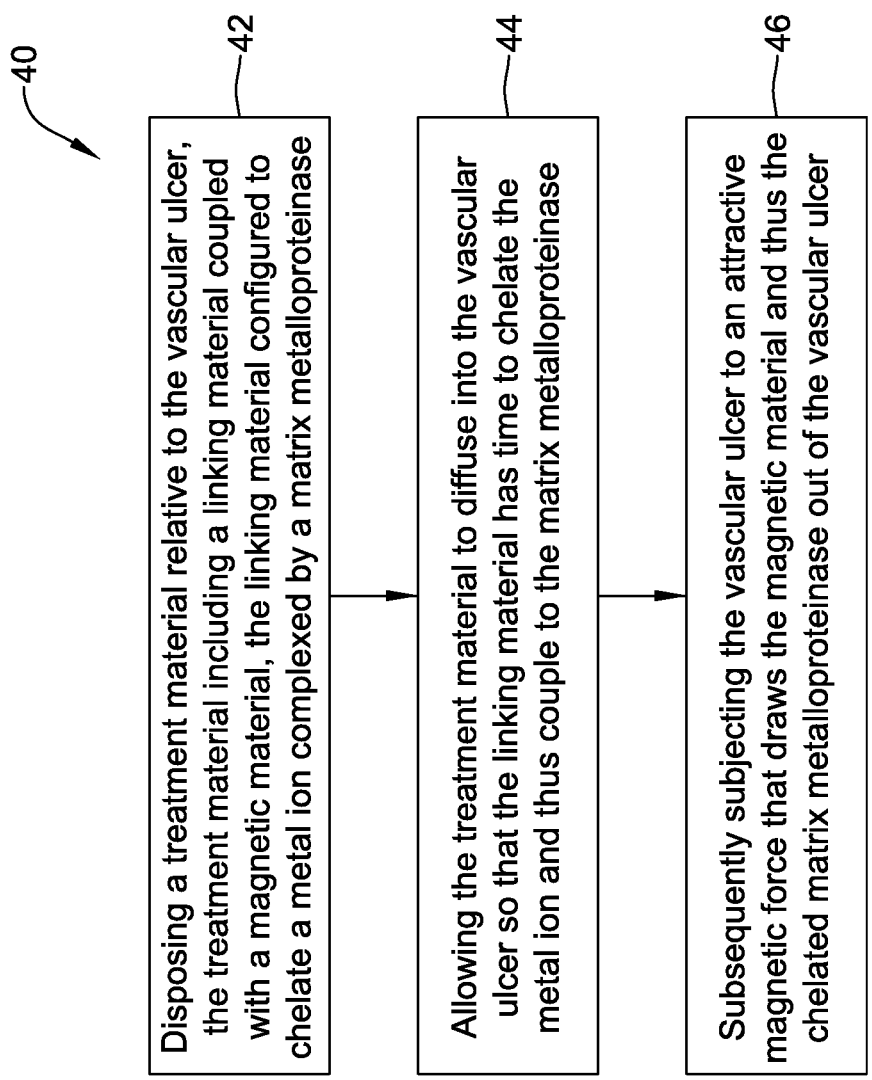
FIG. 8 is a flow diagram showing an illustrative method of treating a vascular ulcer.

FIG. 8 is a flow diagram showing an illustrative but non-limiting example of a method 40 of treating a vascular ulcer in which enzymatic activity by MMPs contributes to formation and/or worsening of the vascular ulcer. In some cases, as generally seen at block 42, a treatment material may be disposed relative to the vascular ulcer, the treatment material including a linking material coupled with a magnetic material, the linking material configured to chelate a metal ion complexed by a matrix metalloproteinase. The treatment particles 22 are a non-limiting example of the treatment material.

In some cases, disposing a treatment material relative to the vascular ulcer may include disposing a patch including the treatment material over the vascular ulcer. In some cases, disposing a treatment material relative to the vascular ulcer may include providing a topical gel including the treatment material onto the vascular ulcer. In some instances, disposing a treatment material relative to the vascular ulcer may include providing a flow of a liquid carrier including the treatment material from a reservoir directly to the vascular ulcer. As seen at block 44, the treatment material may be allowed to diffuse into the vascular ulcer so that the linking material has time to chelate the metal ion and thus couple to the MMP. The vascular ulcer may subsequently be subjected to an attractive magnetic force that draws the magnetic material and thus the chelated matrix metalloproteinase out of the vascular ulcer, as indicated at block 46. In some cases, this may include placing a magnet over the vascular ulcer.

Figure 9:
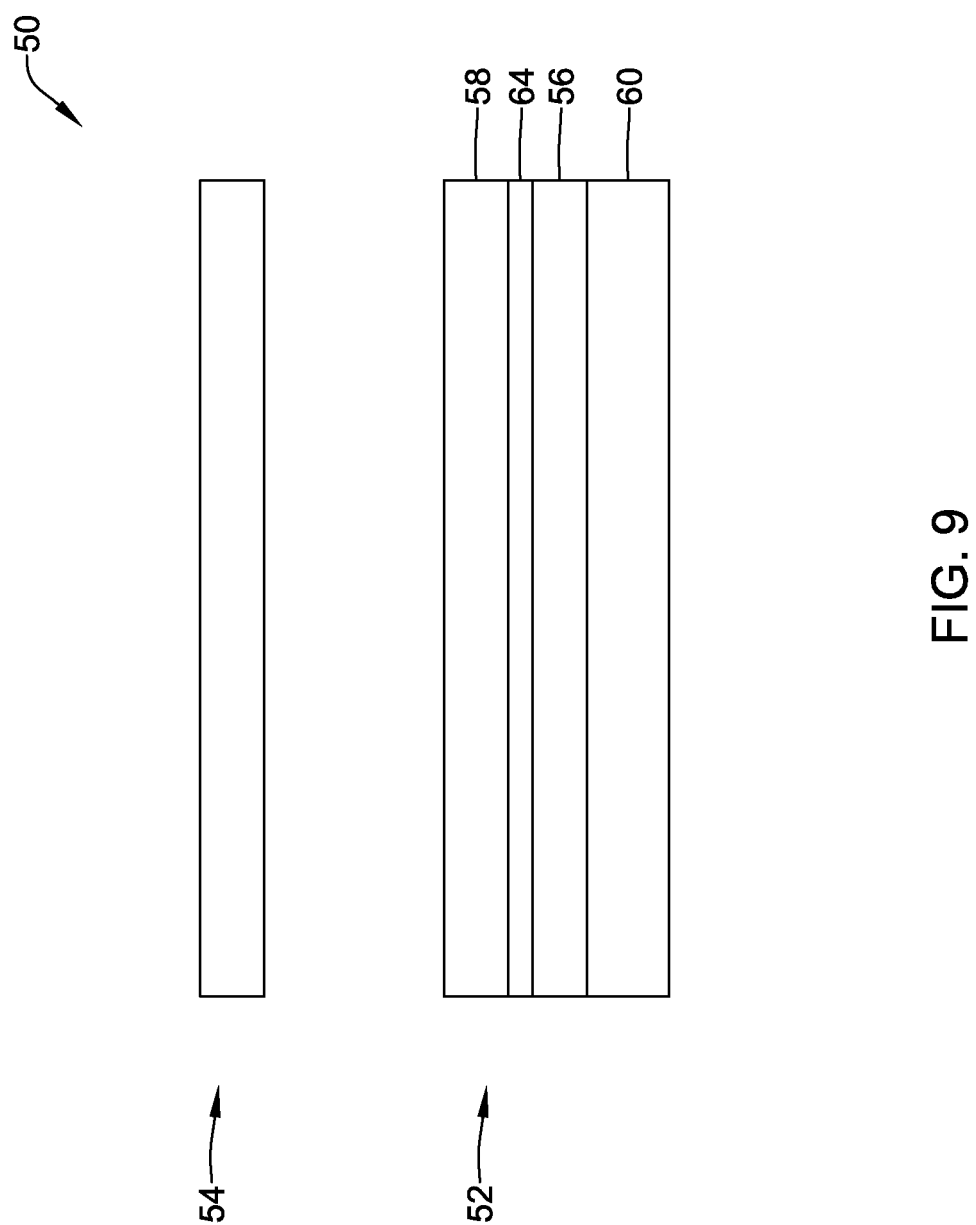
FIG. 9 is a schematic illustration of a vascular ulcer treatment patch in accordance with an example of the disclosure.

FIG. 9 is a schematic view of a kit 50 for treating a vascular ulcer in which enzymatic activity contributes to formation of the vascular ulcer. The kit 50 may be considered as including a first component 52 that is configured to be positioned relative to the vascular ulcer and a second component 54 that is configured to be positioned relative to the vascular ulcer subsequent to application of the first component 52. In some cases, the first component 52 may include a linking material 56 having an affinity for an enzyme involved in formation of the vascular ulcer and a first magnetic material 58 that is coupled to the linking material 56 such that the enzyme within the vascular ulcer can become coupled to the linking material 56 and thus become coupled to the first magnetic material 58. In some cases, the enzyme may be a matrix metalloproteinase, and the linking material 56 may be a chelating agent that is configured to chelate a metal ion complexed by the matrix metalloproteinase. In some cases, the metal ion may include calcium ions or zinc ions, for example. In some cases, the second component 54 may include a second magnetic material 62 that is configured to attract the first magnetic material 58 and thus attract the enzymes (such as MMP) that are coupled to the first magnetic material 58 via the linking material 56.

In some cases, on a molecular scale, the first component 52 may be considered as representing a treatment particle 22 and thus the linking material 56 may represent a linking molecule and the first magnetic 58 may represent a magnetic nanoparticle (MNP). In some cases, the first component 52 may represent a patch, and the linking material 56 and the first magnetic material 58 may each represent large numbers of linking molecules and magnetic nanoparticles, respectively. In some cases, the first magnetic material 56 includes magnetic nanoparticles having a particle diameter in the range of 3 to 50 nanometers.

In some cases, the first component 52 also includes a carrier 60. The carrier 60 may, for example, be a topical gel in which the linking material 56 and the first magnetic material 58 may be dispersed. In some cases, the carrier 60 may be a woven or nonwoven material that forms an adhesive patch. In some cases, the carrier 60 may include a non-planar surface having spikes or other protrusions to help extend the linking material 56 and the first magnetic material 58 further into the vascular ulcer 10. In some cases, for example, the carrier 60 may be dimensioned to at least partially span the vascular ulcer 10. In some cases, the first component 52 may also include an intermediate material 64 that helps to couple the linking material 56 to the first magnetic material 58.

It will be appreciated that a variety of different materials may be used in forming the vascular ulcer treatment patches described herein. In some embodiments, for example, the vascular ulcer treatment patches may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A kit for treating a vascular ulcer in which enzymatic activity of matrix metalloproteinase enzymes contributes to formation of the vascular ulcer, the kit comprising:
    a first component configured to be positioned relative to the vascular ulcer, the first component including:
        a first magnetic material;
        a linking material having an affinity for the matrix metalloproteinase enzyme involved in formation of the vascular ulcer, the linking material comprising ethylenediaminetetracetic acid (EDTA), the EDTA adapted to chelate a calcium or zinc ion complexed by the matrix metalloproteinase, the EDTA bonded to the first magnetic material by an intervening material comprising tetramethylsilane (TMS);
        wherein the matrix metalloproteinase enzyme can become coupled to the linking material and thus become coupled to the first magnetic material; and
    a second component configured to be positioned relative to the vascular ulcer subsequent to application of the first component, the second component including a second magnetic material configured to attract the first magnetic material and attract the enzymes coupled to the first magnetic material via the linking material.

2. The kit of claim 1, wherein the first magnetic material comprises magnetic nanoparticles.

3. The kit of claim 2, wherein the magnetic nanoparticles have an average size range of about 3 to about 50 nanometers (nm).

4. The kit of claim 1, wherein the first component further comprises a carrier, and the linking material is dispersed relative to the carrier.

5. The kit of claim 4, wherein the carrier comprises a topical gel.

6. The kit of claim 4, wherein the carrier comprises a woven or nonwoven material forming an adhesive patch.

7. A kit for treating a vascular ulcer in which enzymatic activity of matrix metalloproteinase enzymes contributes to formation of the vascular ulcer, the kit comprising:
a first component configured to be positioned relative to the vascular ulcer, the first component including:
a first magnetic material;
a linking material having an affinity for the matrix metalloproteinase enzyme involved in formation of the vascular ulcer, the linking material comprising a polydentate chelating agent that is adapted to chelate a metal ion that is complexed by the matrix metalloproteinase, wherein the matrix metalloproteinase enzyme can become coupled to the linking material and thus become coupled to the first magnetic material; and
a second component configured to be positioned relative to the vascular ulcer subsequent to application of the first component, the second component including a second magnetic material configured to attract the first magnetic material and attract the enzymes coupled to the first magnetic material via the linking material.

8. The kit of claim 7, wherein the polydentate chelating agent has one or more binding sites available to couple with the first magnetic material and one or more binding sites available to chelate the metal ion complexed by the matrix metalloproteinase enzymes.

9. The kit of claim 8, wherein the metal ion comprises calcium ion or zinc ion.

10. The kit of claim 7, wherein the polydentate chelating agent comprises

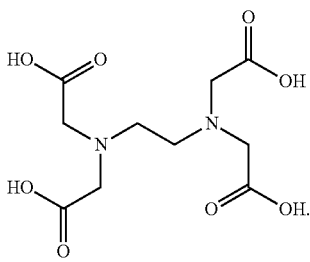

11. The kit of claim 7, wherein the polydentate chelating agent comprises

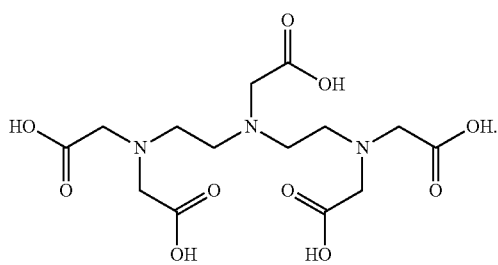 [SMILES: O=C(O)CN(CCN(CC(=O)O)CC(=O)O)CCN(CC(=O)O)CC(=O)O]

12. The kit of claim 7, wherein the polydentate chelating agent comprises

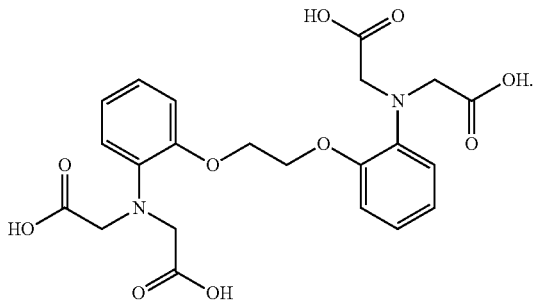 [SMILES: O=C(O)CN(CC(=O)O)c1ccccc1OCCOc1ccccc1N(CC(=O)O)CC(=O)O]

13. The kit of claim 7, wherein the polydentate chelating agent comprises

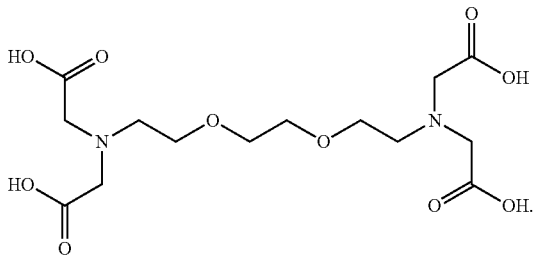 [SMILES: O=C(O)CN(CCOCCOCCN(CC(=O)O)CC(=O)O)CC(=O)O]

14. The kit of claim 7, further comprising an intermediate material that couples the polydentate chelating agent to the first magnetic material, the intermediate material comprising one or more of tetramethoxylsilane (TMS), diethylenetriamine (DETA) salicylaldehyde silica, DETA naphthaldehyde silica, DETA bis-naphthaldehyde silica, DETA bis-salicylaldehyde silica, propylthioethylamine silica, mercapto silica, silicon 3-aminopropyltriethoxysilane, 2,4-D immobilized silica, carboxyhydrazone functionalized silica, 3-hydroxy-2-methyl-1,4-napthaquinone immobilized silica, 5-amino-1,3,4-thiadizole-2-thiol modified silica, aminopropyl silica, and N-5-azido-2-nitrobenzoyloxysuccinimide modified silica.

15. The kit of claim 7, wherein the first magnetic material comprises magnetic nanoparticles.

16. The kit of claim 15, wherein the magnetic nanoparticles have an average size range of about 3 to about 50 nanometers (nm).

17. The kit of claim 7, wherein the first component further comprises a carrier, and the linking material is dispersed relative to the carrier.

18. The kit of claim 17, wherein the carrier comprises a topical gel.

19. The kit of claim 17, wherein the carrier comprises a woven or nonwoven material forming an adhesive patch.

20. The kit of claim 7, wherein the first component is adapted to be provided in a reservoir that is adapted to be placed proximate the vascular ulcer.

* * * * *